United States Patent
Perti

(10) Patent No.: US 8,534,080 B2
(45) Date of Patent: Sep. 17, 2013

(54) COMPOSITIONS COMPRISING IODOTRIFLUOROMETHANE AND USES THEREOF

(75) Inventor: Deepak Perti, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 638 days.

(21) Appl. No.: 12/739,457

(22) PCT Filed: Oct. 31, 2008

(86) PCT No.: PCT/US2008/081955
§ 371 (c)(1),
(2), (4) Date: Apr. 23, 2010

(87) PCT Pub. No.: WO2009/059106
PCT Pub. Date: May 7, 2009

(65) Prior Publication Data
US 2010/0257881 A1    Oct. 14, 2010

Related U.S. Application Data

(60) Provisional application No. 60/984,173, filed on Oct. 31, 2007.

(51) Int. Cl.
*F25B 1/00* (2006.01)

(52) U.S. Cl.
USPC .......................................................... 62/115

(58) Field of Classification Search
USPC ................. 62/84, 77, 114, 115; 252/67, 68
See application file for complete search history.

(56) References Cited

U.S. PATENT DOCUMENTS

| | | | | |
|---|---|---|---|---|
| 4,557,851 A * | 12/1985 | Enjo et al. | ......................... | 252/70 |
| 4,983,312 A * | 1/1991 | Tamura et al. | ................... | 252/67 |
| 5,716,549 A | 2/1998 | Nimitz et al. | | |
| 6,969,701 B2 | 11/2005 | Singh et al. | | |
| 7,074,751 B2 | 7/2006 | Singh et al. | | |
| 8,024,937 B2 * | 9/2011 | Minor | .............................. | 62/115 |
| 2005/0233923 A1 | 10/2005 | Singh et al. | | |
| 2005/0233933 A1 | 10/2005 | Singh et al. | | |
| 2006/0025322 A1 | 2/2006 | Wilson et al. | | |
| 2006/0033071 A1 | 2/2006 | Wilson et al. | | |
| 2006/0116310 A1 | 6/2006 | Singh et al. | | |

FOREIGN PATENT DOCUMENTS

| | | |
|---|---|---|
| EP | 1 028 152 A2 | 8/2000 |
| EP | 1 193 305 A1 | 4/2002 |
| WO | 00/56834 A1 | 9/2000 |
| WO | 2006/069362 A2 | 6/2006 |
| WO | 2007/126760 A2 | 11/2007 |
| WO | 2009/009413 A2 | 1/2009 |

OTHER PUBLICATIONS

PCT International Search Report and Written Opinion dated Mar. 30, 2009.
Lubricants in Refrigeration Systems, 1990 ASHRAE Handbook, Refrigeration Systems and Application, Chapter 8, pp. 8.1-8.21, Atlanta, Georgia.
Synthetic Lubricants and High Performance Fluids, Edited by Ronald L. Shubkin, Chapter 2, Esters, pp. 41-65, Chapter 4, Polyalkylene Glycols, pp. 101-123, Marcel Dekker Inc., 1993, New York, New York.
Saunders and Frisch, Polyurethanes Chemistry and Technology, 1962, vol. I and II, John Wiley & Sons, New York, New York.

* cited by examiner

*Primary Examiner* — Melvin Jones

(57) ABSTRACT

Disclosed are compositions comprising iodotrifluoromethane and other compounds that are useful as heat transfer fluids, including refrigerants, in a stationary air conditioning or refrigeration system, a flooded evaporator chiller or a direct expansion chiller. Also disclosed are methods for producing cooling and methods for replacing R22, R407C, R410A, R404A or R507A in such equipment.

16 Claims, 3 Drawing Sheets

US 8,534,080 B2

COMPOSITIONS COMPRISING IODOTRIFLUOROMETHANE AND USES THEREOF

This application represents a national filing under 35 U.S.C. 371 of International Application No. PCT/US08/81955 filed Oct. 31, 2008, and claims priority of U.S. Provisional Application No. 60/984,173, filed Oct. 31, 2007.

BACKGROUND OF THE INVENTION

1. Field of the Invention

The present disclosure relates to the field of low GWP refrigerant compositions comprising iodotrifluoromethane. These compositions are useful as low GWP replacements in equipment designed for R22, R407c, R410A, R404A or R507A, including stationary air conditioning or refrigeration systems, flooded evaporator chillers or direct expansion chillers.

2. Description of Related Art

Working fluids for various applications are being sought that have little if any environmental impact. The hydrofluorocarbon working fluids adopted as replacements for chlorofluorocarbons, have no ozone depletion potential, but have been found to contribute to global warming.

Therefore, replacements are sought for the hydrofluorocarbons currently in use as refrigerants, heat transfer fluids, cleaning solvents, aerosol propellants, foam blowing agents and fire extinguishing or suppression agents.

In order to serve as drop-in replacements in existing equipment, replacements must be close to or match the properties of the original working fluid for which the equipment was designed. It would be desirable to identify compositions that provide a balance of properties that will allow replacement of existing refrigerants and also to serve as refrigerants in new equipment designed for similar applications.

SUMMARY OF THE INVENTION

The present invention provides for particular iodotrifluoromethane compositions, and in particular, refrigerants for replacing R22, R407c, R410A, R404A or R507A, which particular iodotrifluoromethane compositions have a low global warming potential (GWP) and similar energy efficiency and refrigeration capacity to the refrigerant being replaced. In addition, the present invention provides for refrigerants having low or a specified amount of glide for heat transfer systems with heat exchangers (i.e., evaporators or condensers) that are optimized to take advantage of glide.

In particular, the compositions disclosed herein may be useful for replacing R22, R404A, R407c, R410A, or R507A as a working fluid in a stationary air conditioning or a stationary refrigeration system, or for replacing R22, R407c or R410A in a flooded evaporator chiller or a direct expansion (DX) chiller. Compositions as disclosed herein may be useful in new or existing equipment.

According to the present invention, there is provided a composition comprising iodotrifluoromethane, difluoromethane and an additional compound selected from the group consisting of pentane, butane, isobutane, propylene, cyclopropylene and propane.

In a particular embodiment, the additional compound is propane. In this embodiment, the composition may further comprise pentafluoroethane.

Further in accordance with the present invention, there is provided a composition consisting essentially of either iodotrifluoromethane and 1,1,1,2-tetrafluoroethane; or iodotrifluoromethane, 1,1,1,2-tetrafluoroethane and difluoromethane; or iodotrifluoromethane and pentafluoroethane; or iodotrifluoromethane, difluoromethane, pentafluoroethane and 1,1,1,2-tetrafluoroethane.

Further in accordance with the present invention, there is provided a composition consisting essentially of about 0.01 to about 67.25 weight difluoromethane and about 32.75 to about 99.99% iodotrifluoromethane.

Also in accordance with the present invention, there is provided a method for replacing R22, R407c, R-410A, R404A or R507A in a flooded evaporator chiller, a direct expansion chiller or a stationary air conditioning system or a stationary refrigeration system. The method comprises providing any of the above compositions to a stationary air conditioning system or a stationary refrigeration system, wherein the composition is a refrigerant. According to this method, R22, R404A, R407c, R410A or R507A are replaced by any of the above compositions in a stationary air conditioning or a stationary refrigeration system, and R22, R407c or R410A are replaced by any of the above compositions in a flooded evaporator chiller or a direct expansion chiller.

Further in accordance with the present invention, there is provided a method for producing cooling in either a stationary air conditioning system or a stationary refrigeration system, a flooded evaporator or a direct expansion chiller. The method comprises evaporating any of the compositions above in an evaporator, wherein the composition is a refrigerant, to form a vapor refrigerant, condensing the refrigerant vapor to form a refrigerant liquid, and returning the refrigerant liquid to the evaporator.

In one embodiment, the method for producing cooling comprises producing cooling in a stationary refrigeration or stationary air conditioning system According to another embodiment, the method of producing cooling comprises producing cooling in a flooded evaporator chiller. In this method, a first cooling medium is circulated through an inlet in the evaporator, through a coil in the evaporator and to an outlet of the evaporator, thereby lowering the temperature of the first cooling medium as it passes from the inlet to the outlet of the evaporator. The first cooling medium is then passed to a body to be cooled, thereby producing cooling. This embodiment of the method of the present invention may be practiced in a flooded evaporator chiller.

According to yet another embodiment, the method of producing cooling comprises producing cooling in a direct expansion chiller. In this method, the step of evaporating the refrigerant composition comprises circulating the refrigerant composition through an inlet in the evaporator, through a coil in the evaporator, and through an outlet in the evaporator, thereby lowering the temperature of a first liquid cooling medium contained in the evaporator. The first liquid cooling medium is then passed out of the evaporator to a body to be cooled, thereby producing cooling. This embodiment of the method of the present invention may be practiced in a direct expansion chiller.

DETAILED DESCRIPTION OF THE INVENTION

Figure 1:
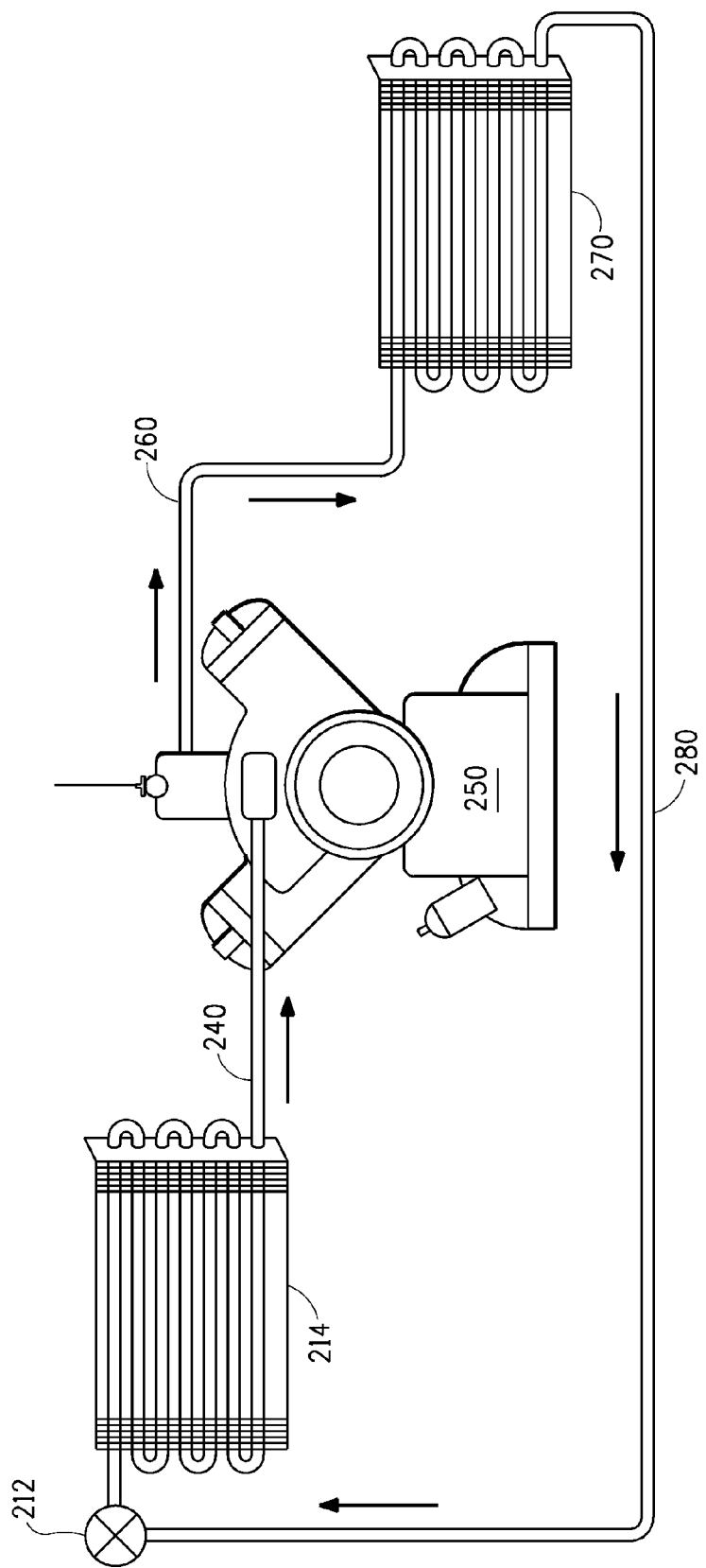
FIG. 1 is a schematic diagram of a stationary air conditioning or a stationary refrigeration system which utilizes the refrigerant compositions of the present invention.

Before addressing details of embodiments described below, some terms are defined or clarified.

Global warming potential (GWP) is an index for estimating relative global warming contribution due to atmospheric emission of a kilogram of a particular greenhouse gas compared to emission of a kilogram of carbon dioxide. GWP can be calculated for different time horizons showing the effect of atmospheric lifetime for a given gas. The GWP for the 100 year time horizon is commonly the value referenced. For mixtures, a weighted average can be calculated based on the individual GWPs for each component.

Refrigeration capacity (sometimes referred to as cooling capacity) is a term to define the change in enthalpy of a refrigerant in an evaporator per pound of refrigerant circulated, i.e., the heat removed by the refrigerant in the evaporator per a given time. The refrigeration capacity is a measure of the ability of a refrigerant or heat transfer composition to produce cooling. Therefore, the higher the capacity the greater the cooling that may be produced.

Coefficient of performance (COP) is the amount of heat removed divided by the required energy input to operate the cycle. The higher the COP, the higher the energy efficiency. COP is directly related to the energy efficiency ratio (EER) that is the efficiency rating for refrigeration or air conditioning equipment at a specific set of internal and external temperatures.

Glide (also sometimes referred to as temperature glide) is defined as the absolute value of the difference between the starting and ending temperatures of a phase change process by a refrigerant within a component of a refrigerating or air conditioning system exclusive of any subcooling or superheating. This term usually describes condensation or evaporation of a zeotrope. Specifically, refrigerant glide in a condenser is the difference between its dew point and bubble point temperatures at the condensing pressure, while in an evaporator, it is the difference between the inlet temperature and the saturated vapor temperature at the evaporating pressure. Pure compound refrigerants have zero glide as do azeotrope compositions at specific temperatures and pressures. Near-azeotrope (sometimes referred to as azeotrope-like) compositions that behave similarly to azeotropes, will have low glide. Compositions that are non-azeotropes (or zeotropes) may have significantly higher glide. Average glide is meant to mean the average of glide in the evaporator and glide in the condenser.

The term "subcooling" refers to the reduction of the temperature of a vapor below that vapor's saturation point for a given pressure. The saturation point is the temperature at which the vapor usually would condense to a liquid, but subcooling produces a lower temperature vapor at the given pressure. By cooling a vapor below the saturation point, the net refrigeration capacity can be increased. Subcooling thereby improves refrigeration capacity and energy efficiency of a system, such as vapor compression heat transfer systems (meaning refrigeration or air conditioning systems). Superheat is a term defines how far above its saturation vapor temperature a vapor composition is heated.

As used herein, a non-azeotropic composition comprises one that is not azeotropic and also not near-azeotropic, meaning that it behaves as a simple mixture of components and thus will fractionate during evaporation or boiling off. During leakage from a heat transfer system this fractionation will cause the lower boiling (higher vapor pressure) component to leak out of the apparatus first. Thus, the vapor pressure of the heat transfer composition remaining inside the heat transfer system will be reduced. This drop in pressure can be measured and used as an early indication of a leak.

As used herein, an azeotropic composition comprises a constant-boiling mixture of two or more substances that behave as a single substance. One way to characterize an azeotropic composition is that the vapor produced by partial evaporation or distillation of the liquid has the same composition as the liquid from which it is evaporated or distilled, i.e., the mixture distills/refluxes without compositional change. Constant-boiling compositions are characterized as azeotropic because they exhibit either a maximum or minimum boiling point, as compared with that of the non-azeotropic mixture of the same compounds. An azeotropic composition will not fractionate within a heat transfer system during operation, which may reduce efficiency of the system. Additionally, an azeotropic composition will not fractionate upon leakage from a heat transfer system.

As used herein, a near-azeotropic composition (also commonly referred to as an "azeotrope-like composition") comprises a substantially constant boiling liquid admixture of two or more substances that behaves essentially as a single substance. One way to characterize a near-azeotropic composition is that the vapor produced by partial evaporation or distillation of the liquid has substantially the same composition as the liquid from which it was evaporated or distilled, that is, the admixture distills/refluxes without substantial composition change. Another way to characterize a near-azeotropic composition is that the bubble point vapor pressure and the dew point vapor pressure of the composition at a particular temperature are substantially the same. Herein, a composition is near-azeotropic if, after 50 weight percent of the composition is removed, such as by evaporation or boiling off, the difference in vapor pressure between the original composition and the composition remaining after 50 weight percent of the original composition has been removed is less than about 10 percent.

As used herein, a heat transfer system may be any refrigeration system, refrigerator, air conditioning system, air conditioner, heat pump, flooded evaporator chiller, direct expansion chiller and the like utilizing a heat transfer composition.

As used herein, a heat transfer composition comprises a composition used to carry heat from a heat source to a heat sink.

As used herein, a refrigerant comprises a compound or mixture of compounds that function as a heat transfer composition in a cycle wherein the composition undergoes a phase change from a liquid to a gas and back.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise. Group numbers corresponding to columns within the Periodic Table of the elements use the "New Notation" convention as seen in the *CRC Handbook of Chemistry and Physics,* 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

Compositions

The present disclosure relates generally to compositions comprising iodotrifluoromethane ($CF_3I$). Iodotrifluoromethane is commercially available from various sources or may be prepared by methods known in the art.

According to one embodiment, the composition of the present invention comprises iodotrifluoromethane ($CF_3I$), difluoromethane (R-32) and at least one hydrocarbon. The compositions of this embodiment will be hereinafter referred to as the compositions of Group A. The additional hydrocarbons are shown in Table 1.

TABLE 1

| Code | Structure | Name | Other designation |
|---|---|---|---|
| | $CH_3CH_2CH_2CH_2CH_3$ | n-pentane | |
| | $CH_3CH_2CH_2CH_3$ | n-butane | |
| i-butane | $CH_3CH(CH_3)CH_3$ | Isobutane | |
| | $CH_3CH(CH_3)CH_2CH_3$ | 2-methylbutane | |

TABLE 1-continued

| Code | Structure | Name | Other designation |
|---|---|---|---|
| HC-1270 | $CH_3CH=CH_2$ | Propylene | R1270 |
| HC-C270 | cyclo-$CH_2CH_2CH_2$— | Cyclopropane | RC270 |
| HC-290 | $CH_3CH_2CH_3$ | Propane | R290 |

The hydrocarbons of Table 1 may be prepared by methods known in the art or are commercially available.

According to one particular embodiment, the additional hydrocarbon may comprise in particular propane. In this embodiment, the composition of the present invention may additionally comprise pentafluoroethane.

Alternatively, the compositions of the present invention may consist essentially of iodotrifluoromethane ($CF_3I$), and at least one hydrofluorocarbon. These hydrofluorocarbons are shown in Table 2. The compositions according to this embodiment may include one or more of the hydrofluorocarbons listed in Table 2.

TABLE 2

| Code | Structure | Name | Other designation |
|---|---|---|---|
| HFC-134a | $CF_3CH_2F$ | 1,1,1,2-tetrafluoroethane | R134a |
| HFC-125 | $CF_3CHF_2$ | pentafluoroethane | R125 |
| HFC-32 | $CH_2F_2$ | Difluoromethane | R32 |

In one embodiment, the composition of the present invention consists essentially of iodotrifluoromethane and 1,1,1,2-tetrafluoroethane.

In another embodiment, the composition of the present invention consists essentially of iodotrifluoromethane, 1,1,1,2-tetrafluoroethane and difluoromethane.

In another embodiment, the composition of the present invention consists essentially of iodotrifluoromethane, 1,1,1,2-tetrafluoroethane, difluoromethane and pentafluoroethane.

In another embodiment, the composition of the present invention consists essentially of iodotrifluoromethane and pentafluoroethane.

Any of the compositions listed in the column titled "Composition" in Table 3 are hereinafter referred to as the compositions of Group B. Specific weight percent ranges for the compositions of Group B of the present invention are given in Table 3. It is within the scope of the present invention to include those ranges which are included within any of the ranges given below.

TABLE 3

| Composition | Range (wt %) | Alternate Range A (wt %) | Alternate Range B (wt %) |
|---|---|---|---|
| $CF_3I/32$ | 32.75-99.9/0.01-67.25 | 40-60/60-40 | 60-99.9/40-0.1 |
| $CF_3I/R32/R125/R290$ | 30-40/0.1-60/1-10/1-10 | 30-40/0.1-55/1-10/1-6 | 30-40/0.1-35/1-10/1-3 |
| $CF_3I/R134a$ | 30-60/70-40 | 30-50/70-50 | |
| $CF_3I/R134a/R32$ | 5-35/5-40/30-70 | 5-35/5-40/30-60 | 5-35/5-40/30-40 |
| $CF_3I/R32/R125/R134a$ | 25-50/0.1-60/0-50/5-50 | 25-50/40-60/5-10/5-50 | 25-50/0.1-40/10-50/5-50 |

The compositions of the present invention may be prepared by any convenient method to combine the desired amounts of the individual components as set forth in Table 3. A preferred method is to weigh the desired component amounts and thereafter combine the components in an appropriate vessel. Agitation may be used, if desired.

Further in accordance with the present invention, there is provided a composition consisting essentially of about 0.01 to about 67.25 weight percent difluoromethane and about 32.75 to about 99.99 weight percent iodotrifluoromethane. The composition of this embodiment is hereinafter referred to as the composition of Group C.

The present invention provides compositions that have zero or low ozone depletion potential and low global warming potential (GWP). The compositions as disclosed herein will have global warming potentials that are less than many hydrofluorocarbon refrigerants currently in use. One aspect of the present invention is to provide a composition with a global warming potential of less than 1000, and less than 500, and in some cases less than 350, or even less than 150, or less than 100, or less than 50.

In addition, non-flammability and low GWP are both desirable properties for compositions when used as refrigerants. R32 and propane (R290) are both known to be flammable compounds. In one embodiment, those compositions provided in Alternate range A of Table 2 that contain these flammable compounds are expected to be non-flammable or less flammable. In another embodiment, those compositions provided in Alternate range B of Table 2 are expected to be non-flammable. Overall, compositions as described in Table 2 have lower GWP than the existing refrigerant compounds or blends they are meant to replace (see Examples 1 and 2 herein).

The compositions of the present invention as disclosed herein may be used in combination with a desiccant in a refrigeration, air-conditioning, or heat pump system to aid in removal of moisture. Desiccants may be composed of activated alumina, silica gel, or zeolite-based molecular sieves. Representative molecular sieves include MOLSIV XH-7, XH-6, XH-9 and XH-11 (UOP LLC, Des Plaines, Ill.). For refrigerants with small molecular size such as HFC-32, XH-11 desiccant is preferred.

The compositions of the present invention may further comprise at lease one lubricant selected from the group consisting of polyalkylene glycols, polyol esters, polyvinylethers, mineral oils, alkylbenzenes, synthetic paraffins, synthetic napthenes, and poly(alpha)olefins.

Lubricants for use with the compositions of the present invention comprise those suitable for use with refrigeration or air-conditioning apparatus. Among these lubricants are those conventionally used in vapor compression refrigeration apparatus utilizing chlorofluorocarbon refrigerants. Such lubricants and their properties are discussed in the 1990 ASHRAE Handbook, Refrigeration Systems and Applications, chapter 8, titled "Lubricants in Refrigeration Systems", pages 8.1 through 8.21, herein incorporated by reference. Lubricants suitable for use with compositions of the present invention may comprise those commonly known as "mineral oils" in the field of compression refrigeration lubrication. Mineral oils comprise paraffins (i.e., straight-chain and branched-carbon-chain, saturated hydrocarbons), naphthenes (i.e. cyclic paraffins) and aromatics (i.e. unsaturated, cyclic hydrocarbons containing one or more rings characterized by alternating double bonds). Lubricants suitable for use with the compositions of the present invention further comprise those commonly known as "synthetic oils" in the field of compression refrigeration lubrication. Synthetic oils comprise alkylaryls (i.e. linear and branched alkyl alkylbenzenes), synthetic paraffins and naphthenes, and poly(alphaolefins). Representative conventional lubricants suitable for use with compositions of the present invention are the commercially available BVM 100 N (paraffinic mineral oil sold by BVA Oils), naphthenic mineral oil commercially available from Crompton Co. under the trademarks Suniso® 3GS and Suniso® 5GS, naphthenic mineral oil commercially available from Pennzoil under the trademark Sontex® 372LT, naphthenic mineral oil commercially available from Calumet Lubricants under the trademark Calumet® RO-30, linear alkylbenzenes commercially available from Shrieve Chemicals under the trademarks Zerol® 75, Zerol® 150 and Zerol® 500, and HAB 22 (branched alkylbenzene sold by Nippon Oil).

Lubricants suitable for use with the compositions of the present invention may further comprise those which have been designed for use with hydrofluorocarbon refrigerants and are miscible with refrigerants of the present invention under compression refrigeration and air-conditioning apparatus' operating conditions. Such lubricants and their properties are discussed in "Synthetic Lubricants and High-Performance Fluids", R. L. Shubkin, editor, Marcel Dekker, 1993. Such lubricants include, but are not limited to, polyol esters (POEs) such as Castrol® 100 (Castrol, United Kingdom), polyalkylene glycols (PAGs) such as RL-488A from Dow (Dow Chemical, Midland, Mich.), polyvinyl ethers (PVEs), and polycarbonates (PCs).

Lubricants used with the compositions of the present invention are selected by considering a given compressor's requirements and the environment to which the lubricant will be exposed.

The compositions of the present invention described herein containing hydrocarbons may provide improved miscibility with conventional refrigeration lubricants, such as mineral oil. Thus, use of these hydrocarbon-containing compositions for retrofit of existing equipment would not require the costly and time consuming lubricant change out process.

The compositions of the present invention may further comprise an additive selected from the group consisting of compatibilizers, UV dyes, solubilizing agents, tracers, stabilizers, perfluoropolyethers (PFPE), and functionalized perfluoropolyethers.

The compositions of the present invention may further comprise about 0.01 weight percent to about 5 weight percent of a stabilizer, free radical scavenger or antioxidant. Such other additives include but are not limited to, nitromethane, hindered phenols, hydroxylamines, thiols, phosphites, or lactones. Single additives or combinations may be used.

Optionally, certain refrigeration or air-conditioning system additives may be added, as desired, to compositions of the present invention in order to enhance performance and system stability. These additives are known in the field of refrigeration and air-conditioning, and include, but are not limited to, anti wear agents, extreme pressure lubricants, corrosion and oxidation inhibitors, metal surface deactivators, free radical scavengers, and foam control agents. In general, these additives may be present in the inventive compositions in small amounts relative to the overall composition. Typically concentrations of from less than about 0.1 weight percent to as much as about 3 weight percent of each additive are used. These additives are selected on the basis of the individual system requirements. These additives include members of the triaryl phosphate family of EP (extreme pressure) lubricity additives, such as butylated triphenyl phosphates (BTPP), or other alkylated triaryl phosphate esters, e.g. Syn-O-Ad 8478 from Akzo Chemicals, tricresyl phosphates and related compounds. Additionally, the metal dialkyl dithiophosphates (e.g., zinc dialkyl dithiophosphate (or ZDDP), Lubrizol 1375 and other members of this family of chemicals may be used in compositions of the present invention. Other antiwear additives include natural product oils and asymmetrical polyhydroxyl lubrication additives, such as Synergol TMS (International Lubricants). Similarly, stabilizers such as antioxidants, free radical scavengers, and water scavengers may be employed. Compounds in this category can include, but are not limited to, butylated hydroxytoluene (BHT), epoxides, and mixtures thereof. Corrosion inhibitors include dodeceyl succinic acid (DDSA), amine phosphate (AP), oleoyl sarcosine, imidazone derivatives and substituted sulfphonates. Metal surface deactivators include areoxalyl bis(benzylidene)hydrazide (CAS reg. no. 6629-10-3), N,N'-bis(3,5-di-tert-butyl-4-hydroxyhydrocinnamoylhydrazine (CAS reg no. 32687-78-8), 2,2,'-oxamidobis-ethyl-(3,5-di-tert-butyl-4-hydroxyhydrocinnamate (CAS reg no. 70331-94-1), N,N'-(disalicyclidene)-1,2-diaminopropane (CAS reg no. 94-91-7) and ethylenediaminetetra-acetic acid (CAS reg no. 60-00-4) and its salts, and mixtures thereof.

Additional additives include stabilizers comprising at least one compound selected from the group consisting of hindered phenols, thiophosphates, butylated triphenylphosphorothionates, organophosphates, or phosphites, aryl alkyl ethers, terpenes, terpenoids, epoxides, fluorinated epoxides, oxetanes, ascorbic acid, thiols, lactones, thioethers, amines, nitromethane, alkylsilanes, benzophenone derivatives, aryl sulfides, divinyl terephthalic acid, diphenyl terephthalic acid, ionic liquids, and mixtures thereof. Representative stabilizer compounds include but are not limited to tocopherol; hydroquinone; t-butyl hydroquinone; monothiophosphates; and dithiophosphates, commercially available from Ciba Specialty Chemicals, Basel, Switzerland, hereinafter "Ciba", under the trademark Irgalube® 63; dialkylthiophosphate esters, commercially available from Ciba under the trademarks Irgalube® 353 and Irgalube® 350, respectively; butylated triphenylphosphorothionates, commercially available from Ciba under the trademark Irgalube® 232; amine phosphates, commercially available from Ciba under the trademark Irgalube® 349 (Ciba); hindered phosphites, commercially available from Ciba as Irgafos® 168; a phosphate such as (Tris-(di-tert-butylphenyl), commercially available from Ciba under the trademark Irgafos® OPH; (Di-n-octyl phosphite); and iso-decyl diphenyl phosphite, commercially available from Ciba under the trademark Irgafos® DDPP; anisole; 1,4-dimethoxybenzene; 1,4-diethoxybenzene; 1,3,5-trimethoxybenzene; d-limonene; retinal; pinene; menthol; Vitamin A; terpinene; dipentene; lycopene; beta carotene; bornane; 1,2-propylene oxide; 1,2-butylene oxide; n-butyl glycidyl ether; trifluoromethyloxirane; 1,1-bis(trifluoromethyl)oxirane; 3-ethyl-3-hydroxymethyl-oxetane, such as OXT-101 (Toagosei Co., Ltd); 3-ethyl-3-((phenoxy)methyl)-oxetane, such as OXT-211 (Toagosei Co., Ltd); 3-ethyl-3-((2-ethyl-hexyloxy)methyl)-oxetane, such as OXT-212 (Toagosei Co., Ltd); ascorbic acid; methanethiol (methyl mercaptan); ethanethiol (ethyl mercaptan); Coenzyme A; dimercaptosuccinic acid (DMSA); grapefruit mercaptan ((R)-2-(4-methylcyclohex-3-enyl)propane-2-thiol)); cysteine ((R)-2-amino-3-sulfanyl-propanoic acid); lipoamide (1,2-dithiolane-3-pentanamide); 5,7-bis(1,1-dimethylethyl)-3-[2,3(or 3,4)-dimethylphenyl]-2(3H)-benzofuranone, commercially available from Ciba under the trademark Irganox® HP-136; benzyl phenyl sulfide; diphenyl sulfide; diisopropylamine; dioctadecyl 3,3'-thiodipropionate, commercially available from Ciba under the trademark Irganox® PS 802 (Ciba); didodecyl 3,3'-thiopropionate, commercially available from Ciba under the trademark Irganox® PS 800; di-(2,2,6,6-tetramethyl-4-piperidyl)sebacate, commercially available from Ciba under the trademark Tinuvin® 770; poly-(N-hydroxyethyl-2,2,6,6-tetramethyl-4-hydroxy-piperidyl succinate, commercially available from Ciba under the trademark Tinuvin® 622LD (Ciba); methyl bis tallow amine; bis tallow amine; phenol-alpha-naphthylamine; bis(dimethylamino)methylsilane (DMAMS); tris(trimethylsilyl)silane (TTMSS); vinyltriethoxysilane; vinyltrimethoxysilane; 2,5-difluorobenzophenone; 2',5'-dihydroxyacetophenone; 2-aminobenzophenone; 2-chlorobenzophenone; benzyl phenyl sulfide; diphenyl sulfide; dibenzyl sulfide; ionic liquids; and others as disclosed in International Patent Application No. PCT/US07/07477, filed Mar. 26, 2007.

Ionic liquid stabilizers comprise at least one ionic liquid. Ionic liquids are organic salts that are liquid at room temperature (approximately 25° C.). In another embodiment, ionic liquid stabilizers comprise salts containing cations selected from the group consisting of pyridinium, pyridazinium, pyrimidinium, pyrazinium, imidazolium, pyrazolium, thiazolium, oxazolium and triazolium; and anions selected from the group consisting of $[BF_4]-$, $[PF_6]-$, $[SbF_6]-$, $[CF_3SO_3]-$, $[HCF_2CF_2SO_3]-$, $[CF_3HFCCF_2SO_3]-$, $[HCClFCF_2SO_3]-$, $[(CF_3SO_2)_2N]-$, $[(CF_3CF_2SO_2)_2N]-$, $[(CF_3SO_2)_3C]-$, $[CF_3CO_2]-$, and $F-$. Representative ionic liquid stabilizers include emim $BF_4$ (1-ethyl-3-methylimidazolium tetrafluoroborate); bmim $BF_4$ (1-butyl-3-methylimidazolium tetraborate); emim $PF_6$ (1-ethyl-3-methylimidazolium hexafluorophosphate); and bmim $PF_6$ (1-butyl-3-methylimidazolium hexafluorophosphate), all of which are available from Fluka (Sigma-Aldrich).

The compositions of the present invention may also include as additives perfluoropolyethers which are miscible with hydrofluorocarbon refrigerants or heat transfer fluids. A common characteristic of perfluoropolyethers is the presence of perfluoroalkyl ether moieties. Perfluoropolyether is synonymous to perfluoropolyalkylether. Other synonymous terms frequently used include "PFPE", "PFAE", "PFPE oil", "PFPE fluid", and "PFPAE". For example, Krytox®, available from DuPont, is a perfluoropolyether having the formula of $CF_3-(CF_2)_2-O-[CF(CF_3)-CF_2-O]j'-R'$ f. In the formula, j' is 2-100, inclusive and R' f is $CF_2CF_3$, a C3 to C6 perfluoroalkyl group, or combinations thereof.

Other PFPE's, including the PFPE fluids sold under the trademarks Fomblin® and Galden®, available from Ausimont, Milan, Italy and produced by perfluoroolefin photooxidation, can also be used. Fomblin®$^Y$ can have the formula of $CF_3O(CF_2CF(CF_3)-O-)_{m'}(CF_2-O-)_{n'}-R_{1f'}$ Also suitable is $CF_3O[CF_2CF(CF_3)O]_{m'}(CF_2CF_2O)_{o'}(CF_2O)_{n'}-R_{1f'}$ In the formulae $R_{1f}$ is $CF_3$, $C_2F_5$, $C_3F_7$, or combinations of two or more thereof; (m'+n') is 8-45, inclusive; and m/n is 20-1000, inclusive; o' is 1; (m'+n'+o') is 8-45, inclusive; m'/n' is 20-1000, inclusive.

Fomblin®-Z can have the formula of $CF_3O(CF_2CF_2-O-)_{p'}(CF_2-O)_{q'}CF_3$ where (p'+q') is 40-180 and p'/q' is 0.5-2, inclusive.

Another family of PFPE fluids, available from Daikin Industries, Japan, under the trademark Demnum™, can also be used as additives. Such PFPE fluids can be produced by sequential oligomerization and fluorination of 2,2,3,3-tetrafluorooxetane, yielding the formula of $F-[(CF_2)_3-O]_{t'}-R_{2f'}$ where $R_{2f}$ is $CF_3$, $C_2F_5$, or combinations thereof and t' is 2-200, inclusive.

The two end groups of the perfluoropolyether, independently, can be functionalized or unfunctionalized. In an unfunctionalized perfluoropolyether, the end group can be branched or straight chain perfluoroalkyl radical end groups.

Examples of such perfluoropolyethers can have the formula of $C_{r'}F_{(2r'+1)}$—A—$C_{r'}F_{(2r'+1)}$ in which each r' is independently 3 to 6; A can be O—(CF(CF$_3$)CF$_2$—O)$_{w'}$, O—(CF$_2$—O)$_{x'}$(CF$_2$CF$_2$—O)$_{y'}$, O—(C$_2$F$_4$—O)$_{w'}$, O—(C$_2$F$_4$—O)$_{x'}$(C$_3$F$_6$—O)$_{y'}$, O—(CF(CF$_3$)CF$_2$—O)$_{x'}$(C$_2$F$_4$—O)$_{y'}$, O—(CF$_2$CF$_2$CF$_2$—O)$_{w'}$, O—(CF(CF$_3$)CF$_2$—O)$_{x'}$(CF$_2$CF$_2$—O)$_{y'}$, O—(CF$_2$—O)$_z$, or combinations of two or more thereof; preferably A is O—(CF(CF$_3$)CF$_2$—O)$_9$, O—(C$_2$F$_4$—O)$_{w'}$, O—(C$_2$F$_4$—O)$_x$(C$_3$F$_6$—O)$_{y'}$, O—(CF$_2$CF$_2$CF$_2$—O)$_{w'}$, or combinations of two or more thereof; w' is 4 to 100; x' and y' are each independently 1 to 100. Specific examples include, but are not limited to, F(CF(CF$_3$))—CF$_2$—O)$_9$—CF$_2$CF$_3$, F(CF(CF$_3$))—CF$_2$—O)$_9$—CF(CF$_3$)$_2$, and combinations thereof. In such PFPE's, up to 30% of the halogen atoms can be halogens other than fluorine, such as, for example, chlorine atoms.

The two end groups of the perfluoropolyether, independently, can also be functionalized. A typical functionalized end group can be selected from the group consisting of esters, hydroxyls, amines, amides, cyanos, carboxylic acids and sulfonic acids.

Representative ester end groups include —COOCH$_3$, —COOCH$_2$CH$_3$, —CF$_2$COOCH$_3$, —CF$_2$COOCH$_2$CH$_3$, —CF$_2$CF$_2$COOCH$_3$, —CF$_2$CF$_2$COOCH$_2$CH$_3$, —CF$_2$CH$_2$COOCH$_3$, —CF$_2$CF$_2$CH$_2$COOCH$_3$, —CF$_2$CH$_2$CH$_2$COOCH$_3$, —CF$_2$CF$_2$CH$_2$CH$_2$COOCH$_3$.

Representative hydroxyl end groups include —CF$_2$OH, —CF$_2$CF$_2$OH, —CF$_2$CH$_2$OH, —CF$_2$CF$_2$CH$_2$OH, —CF$_2$CH$_2$CH$_2$OH, —CF$_2$CF$_2$CH$_2$CH$_2$OH.

Representative amine end groups include —CF$_2$NR$^1$R$^2$, —CF$_2$CF$_2$NR$^1$R$^2$, —CF$_2$CH$_2$NR$^1$R$^2$, —CF$_2$CF$_2$CH$_2$NR$^1$R$^2$, —CF$_2$CH$_2$CH$_2$NR$^1$R$^2$, —CF$_2$CF$_2$CH$_2$CH$_2$NR$^1$R$^2$, wherein R$^1$ and R$^2$ are independently H, CH$_3$, or CH$_2$CH$_3$.

Representative amide end groups include —CF$_2$C(O)NR$^1$R$^2$, —CF$_2$CF$_2$C(O)NR$^1$, R$^2$, —CF$_2$CH$_2$C(O)NR$^1$, R$^2$, —CF$_2$CF$_2$CH$_2$C(O)NR$^1$, R$^2$, —CF$_2$CH$_2$CH$_2$C(O)NR$^1$, R$^2$, —CF$_2$CF$_2$CH$_2$CH$_2$C(O)NR$^1$R$^2$, wherein R$^1$ and R$^2$ are independently H, CH$_3$, or CH$_2$CH$_3$.

Representative cyano end groups include —CF$_2$CN, —CF$_2$CF$_2$CN, —CF$_2$CH$_2$CN, —CF$_2$CF$_2$CH$_2$CN, —CF$_2$CH$_2$CH$_2$CN, —CF$_2$CF$_2$CH$_2$CH$_2$CN.

Representative carboxylic acid end groups include —CF$_2$COOH, —CF$_2$CF$_2$COOH, —CF$_2$CH$_2$COOH, —CF$_2$CF$_2$CH$_2$COOH, —CF$_2$CH$_2$CH$_2$COOH, —CF$_2$CF$_2$CH$_2$CH$_2$COOH.

Representative sulfonic acid end groups include —S(O)(O)OR$^3$, —S(O)(O)R$^4$, —CF$_2$OS(O)(O)OR$^3$, —CF$_2$CF$_2$OS(O)(O)OR$^3$, —CF$_2$CH$_2$OS(O)(O)OR$^3$, —CF$_2$CF$_2$CH$_2$OS(O)(O)OR$^3$, —CF$_2$CH$_2$CH$_2$OS(O)(O)OR$^3$, —CF$_2$CF$_2$CH$_2$CH$_2$OS(O)(O)OR$^3$, —CF$_2$S(O)(O)OR$^3$, —CF$_2$CF$_2$S(O)(O)OR$^3$, —CF$_2$CH$_2$S(O)(O)OR$^3$, —CF$_2$CF$_2$CH$_2$S(O)(O)OR$^3$, —CF$_2$CH$_2$CH$_2$S(O)(O)OR$^3$, —CF$_2$CF$_2$CH$_2$CH$_2$S(O)(O)OR$^3$, —CF$_2$OS(O)(O)R$^4$, —CF$_2$CF$_2$O S(O)(O)R$^4$, —CF$_2$CH$_2$OS(O)(O)R$^4$, —CF$_2$CF$_2$CH$_2$O S(O)(O)R$^4$, —CF$_2$CH$_2$CH$_2$O S(O)(O)R$^4$, —CF$_2$CF$_2$CH$_2$CH$_2$O S(O)(O)R$^4$, wherein R$^3$ is H, CH$_3$, CH$_2$CH$_3$, CH$_2$CF$_3$, CF$_3$, or CF$_2$CF$_3$, R$^4$ is CH$_3$, CH$_2$CH$_3$, CH$_2$CF$_3$, CF$_3$, or CF$_2$CF$_3$.

In one embodiment, the compositions of the present invention (meaning those of Groups A, B and C) may be used as blowing agents for use in preparing foams. Thus, according to the present invention, there is provided a foam prepared from such blowing agents, and preferably polyurethane and polyisocyanate foams, and a method of preparing such foams. In such foam embodiments, one or more of the compositions of the present invention is included as a blowing agent and is added to a foamable composition, and the foamable composition is reacted under conditions effective to form a foam. Such conditions may include the use of one or more additional components capable of reacting and foaming under the proper conditions to form a foam or cellular structure. Any of the methods well known in the art, such as those described in "Polyurethanes Chemistry and Technology," Volumes I and II, Saunders and Frisch, 1962, John Wiley and Sons, New York, N.Y., may be used or adapted for use in accordance with the foam embodiments of the present invention.

In another embodiment, the compositions of the present invention may be used as propellants in sprayable compositions. In this embodiment, the present invention relates to a sprayable composition comprising the compositions of the present invention. In this embodiment, the sprayable composition may further comprise an active ingredient to be sprayed together with inert ingredients, solvents and other materials. The sprayable composition may be an aerosol. Suitable active ingredients to be sprayed include, without limitations, cosmetic materials, such as deodorants, perfumes, hair sprays, cleaners, and polishing agents as well as medicinal materials such as anti-asthma and anti-halitosis medications.

The present disclosure also provides a process for producing aerosol products comprising the step of adding a composition of the present invention to an active ingredient in an aerosol container, wherein said composition functions as a propellant.

In one embodiment, a sterilant is an azeotrope or azeotrope-like composition comprising ethylene oxide and a composition of Group A, Group B or Group C. In another embodiment, a sterilant mixture is a non-azeotrope (or zeotrope) composition comprising ethylene oxide and a composition of Group A, Group B or Group C.

In another embodiment, the compositions of the present invention may be used as sterilants. The sterilant may be used to sterilize a great many articles, including but not limited to medical equipment and materials, such diagnostic endoscopes, plastic goods such as syringes, gloves, test tubes, incubators and pacemakers; rubber goods such as tubing, catheters and sheeting; instruments such as needles, scalpels and oxygen tests; and other items such as dilators, pumps, motors and intraocular lenses. In another embodiment, the sterilant of this invention may be used as a fumigant for items outside the medical field, including but not limited to certain food stuffs, such as species, and other items such as furs, bedding, paper goods, and transportation equipment such as the cargo area of airplanes, trains, and ships. The sterilant may be effective against all forms of life, particularly unwanted insects, bacteria, virus, molds, fungi, and other microorganisms.

In one embodiment, a sterilant is an azeotrope or azeotrope-like composition comprising ethylene oxide and a composition of the present invention. In another embodiment, a sterilant is a non-azeotrope (or zeotrope) composition comprising ethylene oxide and a composition of the present invention.

The present invention also provides a method for sterilizing an article which comprises contacting the article with a sterilant comprising ethylene oxide and a composition of the present invention. In one embodiment, the method of sterilizing an article may be accomplished in any manner known in the art, including contacting the article to be sterilized with the sterilant under conditions and for a period of time as to be effective in achieving the desired degree of sterility. In another embodiment, the method is effected by placing the articles to be sterilized in a vessel, evacuating the air from the vessel, humidifying the vessel, and contacting the articles to the sterilant for an effective period of time. In one embodiment the humidifying creates a relative humidity within the vessel of from about 30 to about 80 percent. An effective period of time for sterilizing will depend upon a number of factors including temperature, pressure, relative humidity, the specific sterilant mixture employed and the material being sterilized. Alternatively, some porous articles may require shorter contact times than do articles sealed in polyethylene bags. Further, in another embodiment, certain bacteria are especially resistant and may thus require longer contact times for sterilization.

The compositions of the present invention (meaning the compositions of Groups A, B and C) are particularly useful as refrigerants. The use of such refrigerants in cooling systems and in methods for producing cooling will be described below.

Cooling Systems

FIG. 1 is a schematic illustration of a stationary refrigeration or a stationary air conditioning system which may employ the compositions of the present invention. In this system, liquid refrigerant flows through an expansion valve 212, from which the refrigerant exits as part liquid and part vapor, into an evaporator 214, which has an inlet and an outlet. The liquid refrigerant is vaporized in the evaporator, exiting as a vapor, and enters a suction line 240. The refrigerant vapor is then drawn into a coupled compressor 250, which increases the pressure and temperature of the refrigerant vapor. The compressor compresses this vapor so that it may be condensed at a higher pressure and temperature than the pressure and temperature of the refrigerant vapor when it comes out of the evaporator. The refrigerant vapor flows out of the compressor into a coupled hot gas line 260, and then flows into a condenser 270, whereby the refrigerant vapor is condensed and returned to the liquid phase. A liquid refrigerant line 280 returns the liquid refrigerant to the expansion valve, and the cycle is repeated.

The compositions of the present invention may also be useful in other air conditioning/refrigeration systems, such as small coolers which have less than 5 to 10 kW cooling capacity, or in closed loop heat transfer systems, which re-use refrigerant in multiple steps to produce a cooling effect in one step and a heating effect in a different step. Such systems are typically used in mobile air conditioning systems. As used herein, a mobile air conditioning system refers to any refrigeration or air-conditioning apparatus incorporated into a transportation unit for the road, rail, sea or air.

Figure 2:
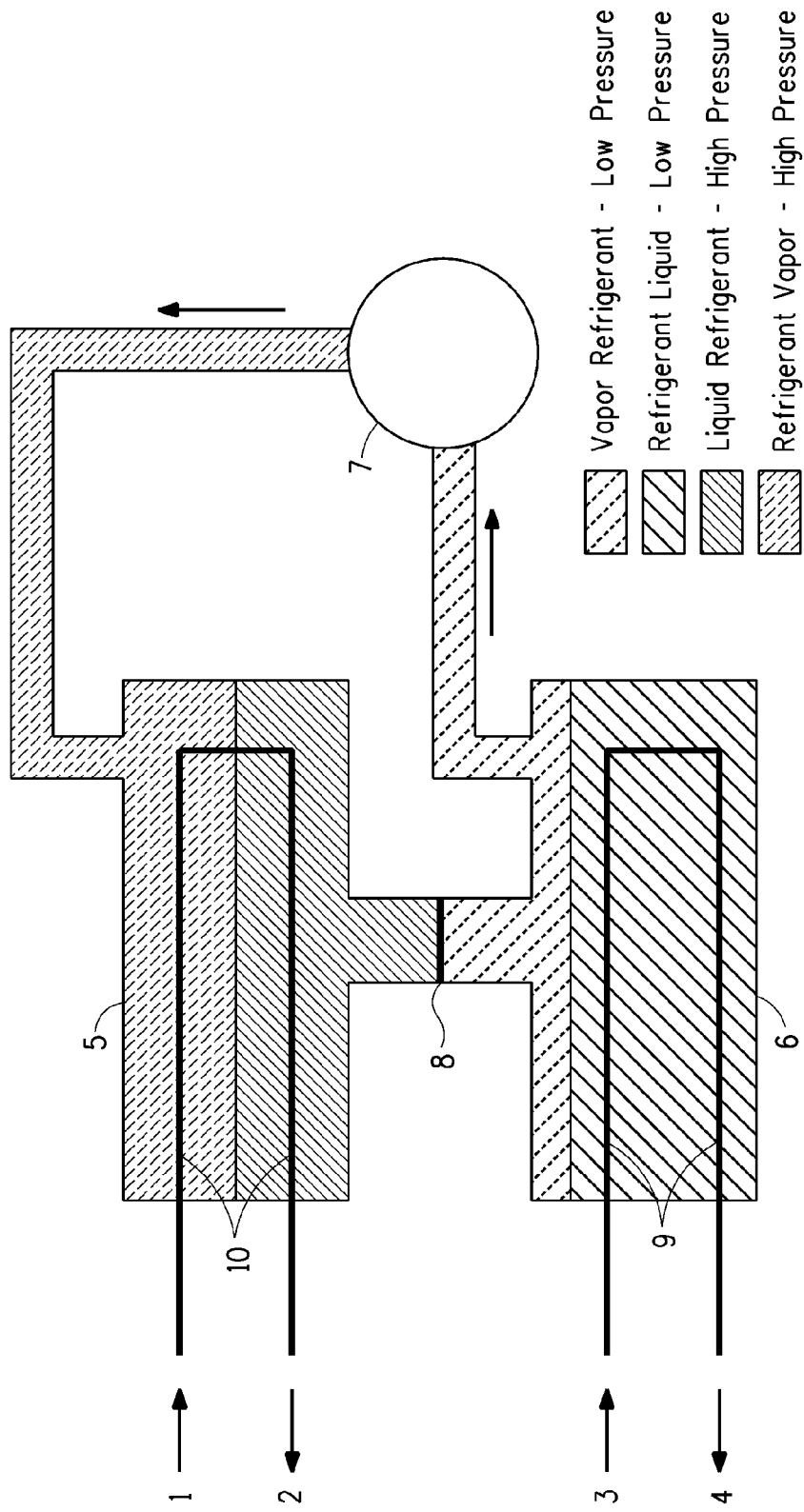
FIG. 2 is a schematic diagram of a flooded evaporator chiller which utilizes the refrigerant compositions of the present invention.
Figure 3:
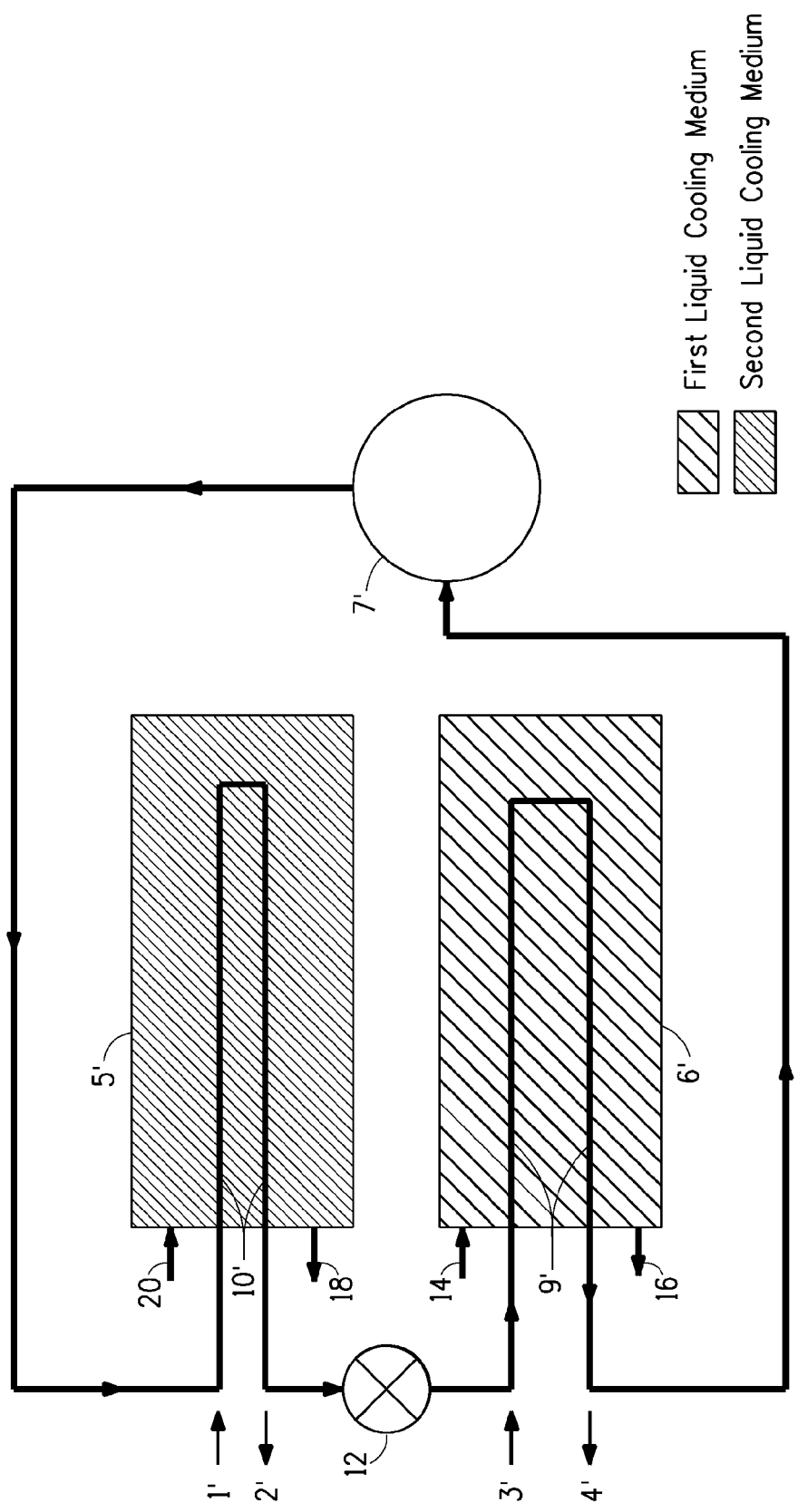
FIG. 3 is a schematic diagram of a direct expansion chiller which utilizes the refrigerant compositions of the present invention.

In another embodiment, the compositions of the present invention may be used as refrigerants in a chiller. A chiller is a type of air conditioning/refrigeration apparatus. Two types of water chillers are available, vapor-compression chillers and absorption chillers. The present disclosure is directed to a vapor compression chiller. Such vapor compression chiller may be either a flooded evaporator chiller, which is shown in FIG. 2, or a direct expansion chiller, which is shown in FIG. 3. Both a flooded evaporator chiller or a direct expansion chiller may be air-cooled or water-cooled. In the embodiment where chillers are water cooled, such chillers are generally associated with cooling towers for heat rejection from the system. In the embodiment where chillers are air-cooled, the chillers are equipped with refrigerant-to-air finned-tube condenser coils and fans to reject heat from the system. Air-cooled chiller systems are generally less costly than equivalent-capacity water-cooled chiller systems including cooling tower and water pump. However, water-cooled systems can be more efficient under many operating conditions due to lower condensing temperatures.

Chillers, including both flooded evaporator and direct expansion chillers, may be coupled with an air handling and distribution system to provide comfort air conditioning (cooling and dehumidifying the air) to large commercial buildings, including hotels, office buildings, shopping centers, hospitals, universities and the like. In another embodiment, chillers, most likely air-cooled direct expansion chillers, have found additional utility in naval submarines and surface vessels.

To illustrate how chillers operate, reference is made to the Figures. A water-cooled, flooded evaporator chiller is shown illustrated in FIG. 2. In this chiller a warm first liquid cooling medium liquid, (usually water, but may have additives, such as glycol) enters the chiller from a cooling system, such as a building cooling system, shown entering at arrow 3, through a coil 9 in an evaporator 6, which has an inlet and an outlet. The warm first liquid cooling medium is delivered to the evaporator, where it is chilled by liquid refrigerant, which is shown in the lower portion of the evaporator. The liquid refrigerant evaporates at a lower temperature than the warm first liquid cooling medium which flows through coil 9. The chilled first liquid cooling medium re-circulates back to the building cooling system, as shown by arrow 4, via a return portion of coil 9. The liquid refrigerant, shown in the lower portion of evaporator 6 in FIG. 2, vaporizes and is drawn into a compressor 7, which increases the pressure and temperature of the refrigerant vapor. The compressor compresses this vapor so that it may be condensed in a condenser 5 at a higher pressure and temperature than the pressure and temperature of the refrigerant vapor when it comes out of the evaporator. A second cooling medium, which is a liquid in the case of a water-cooled chiller, enters the condenser via a coil 10 in condenser 5 from a cooling tower at arrow 1 in FIG. 2. The second cooling medium is warmed in the process and returned via a return loop of coil 10 and arrow 2 to a cooling tower. This second cooling medium cools the vapor in the condenser and turns the vapor to liquid refrigerant, so that there is liquid refrigerant in the lower portion of the condenser as shown in FIG. 2. The condensed liquid refrigerant in the condenser flows back to the evaporator through an expansion device or an orifice 8, and the cycle is repeated. Orifice 8 reduces the pressure of the liquid refrigerant, and converts the liquid refrigerant partially to vapor, that is to say that the liquid refrigerant partially changes to vapor (flashes) as pressure drops between the condenser and the evaporator. Flashing cools the refrigerant both the liquid and vapor to the saturated temperature at evaporator pressure, so that both liquid refrigerant and refrigerant vapor are present in the evaporator.

It should be noted that for a single component refrigerant composition, the composition of the vapor refrigerant in the evaporator is the same as the composition of the liquid refrigerant in the evaporator. In this case, evaporation will occur at a constant temperature. However, if a refrigerant blend is used, as in the case of the compositions of the present invention, the liquid refrigerant and the refrigerant vapor in the evaporator (or in the condenser) may have different compositions. Such compositions depend on the properties of the components such as boiling points, structures and ability to form azeotropes, etc.

Chillers with capacities above 700 kW generally employ flooded evaporators, where the refrigerant is contained in the evaporator and the condenser (i.e., on the shell side). Flooded evaporators require higher charges of refrigerant, but permit closer approach temperatures and higher efficiencies. Chillers with capacities below 700 kW commonly employ evaporators with refrigerant flowing inside the tubes and chilled cooling medium in the evaporator and the condenser, i.e., on the shell side. Such chillers are called direct-expansion (DX) chillers. A water-cooled direct expansion chiller is illustrated in FIG. 3. In the chiller as illustrated in FIG. 3, a first liquid cooling medium, which is a warm liquid, such as warm water, enters an evaporator 6' at inlet 14. Mostly liquid refrigerant enters a coil 9' in the evaporator at arrow 3' and evaporates. As a result, the first liquid cooling medium is cooled in the evaporator, and a cooled first liquid cooling medium exits the evaporator at outlet 16, and is sent to a body to be cooled, such as a building. In this embodiment of FIG. 3, this first liquid cooling medium is the working fluid that produces cooling. The refrigerant vapor exits the evaporator at arrow 4' and is drawn into a compressor 7', where it is compressed and exits as high temperature, high pressure vapor. This refrigerant vapor enters the condenser through a condenser coil at 1'. The refrigerant vapor is cooled by a second liquid cooling medium in the condenser and becomes a liquid. The second liquid cooling medium enters the condenser through a condenser cooling medium inlet 20, and it extracts heat from the condensed refrigerant vapor, which heats the cooling medium. The second liquid cooling medium exits through the condenser cooling medium outlet 18. The condensed refrigerant liquid exits the condenser and flows through an expansion valve 12, which reduces the pressure of the liquid refrigerant. A small amount of refrigerant vapor, produced as a result of the expansion, enters the evaporator with liquid refrigerant, and the cycle is repeated.

Vapor-compression chillers are identified by the type of compressor they employ. In one embodiment, the compositions of the present invention are useful in chillers, which utilize centrifugal compressors, as will be described below. In another embodiment the compositions of the present invention are useful in chillers which utilize positive displacement compressors, i.e., either reciprocating, screw, or scroll compressors.

A centrifugal compressor uses rotating elements to accelerate the refrigerant radially, and typically includes an impeller and diffuser housed in a casing. Centrifugal compressors usually take fluid in at an impeller eye, or central inlet of a circulating impeller, and accelerate it radially outward. Some static pressure rise occurs in the impeller, but most of the pressure rise occurs in the diffuser section of the casing, where velocity is converted to static pressure. Each impeller-diffuser set is a stage of the compressor. Centrifugal compressors are built with from one to twelve or more stages, depending on the final pressure desired and the volume of refrigerant to be handled.

The pressure ratio, or compression ratio, of a compressor is the ratio of absolute discharge pressure to the absolute inlet pressure. Pressure delivered by a centrifugal compressor is practically constant over a relatively wide range of capacities. The pressure a centrifugal compressor can develop depends on the tip speed of the impeller. Tip speed is the speed of the impeller measured at its tip and is related to the diameter of the impeller and its revolutions per minute. The capacity of the centrifugal compressor is determined by the size of the passages through the impeller. This makes the size of the compressor more dependent on the pressure required than the capacity.

Positive displacement compressors draw vapor into a chamber, and the chamber decreases in volume to compress the vapor. After being compressed, the vapor is forced from the chamber by further decreasing the volume of the chamber to zero or nearly zero.

Reciprocating compressors use pistons driven by a crankshaft. They can be either stationary or portable, can be single or multi-staged, and can be driven by electric motors or internal combustion engines. Small reciprocating compressors from 5 to 30 hp are seen in automotive applications and are typically for intermittent duty. Larger reciprocating compressors up to 100 hp are found in large industrial applications. Discharge pressures can range from low pressure to very high pressure (>5000 psi or 35 MPa).

Screw compressors use two meshed rotating positive-displacement helical screws to force the gas into a smaller space. Screw compressors are usually for continuous operation in commercial and industrial application and may be either stationary or portable. Their application can be from 5 hp (3.7 kW) to over 500 hp (375 kW) and from low pressure to very high pressure (>1200 psi or 8.3 MPa).

Scroll compressors are similar to screw compressors and include two interleaved spiral-shaped scrolls to compress the gas. The output is more pulsed than that of a rotary screw compressor.

For chillers which use scroll compressors or reciprocating compressors, capacities below 150 kW, brazed-plate heat exchangers are commonly used for evaporators instead of the shell-and-tube heat exchangers employed in larger chillers. Brazed-plate heat exchangers reduce system volume and refrigerant charge.

Methods

According to another aspect of the present invention, the compositions of the present invention (meaning the compositions of Groups A, B and C) are useful in methods to produce cooling. In these methods, the compositions of the present invention are refrigerants.

In all of the embodiments as illustrated with respect to FIGS. 1-3, there is provided a method for producing cooling, comprising evaporating the composition of any of Groups A, B or C in an evaporator, wherein the composition is a refrigerant, to form a vapor refrigerant, condensing the vapor refrigerant to form a refrigerant liquid, and returning the refrigerant liquid to the evaporator. In all of the embodiments, the refrigerant vapor may be compressed in order to increase its temperature and pressure before it is condensed.

In one embodiment, the method for producing cooling comprises producing cooling in a stationary refrigeration or stationary air conditioning system as described with respect to FIG. 1 above. This method comprises the steps of evaporating a refrigerant composition of the present invention in an evaporator to form a refrigerant vapor, thereby producing cooling. The refrigerant vapor exits the evaporator and is sent to a compressor, which increases the pressure and temperature of the refrigerant vapor. The refrigerant composition is thereafter condensed to a liquid refrigerant and returned to the evaporator.

In another embodiment, the method for producing cooling comprises producing cooling in a flooded evaporator chiller as described above with respect to FIG. 2. In this method, a refrigerant composition of the present invention is evaporated in an evaporator to form a refrigerant vapor. A first cooling medium, which is a warm liquid, is brought to the evaporator from a cooling system, and is circulated through an inlet of the evaporator, through a coil in the evaporator, and to an outlet of the evaporator, thereby lowering the temperature of the cooling medium as it passes from the inlet to the outlet of the evaporator. The warm first cooling medium is cooled in the evaporator and is passed to a body to be cooled, such as a building, thereby producing cooling. The refrigerant vapor exits the evaporator and is sent to a compressor, which increases the pressure and temperature of the refrigerant vapor. The refrigerant composition is then condensed in a condenser. A second cooling medium, which is a chilled liquid, or air, is transported into the condenser from a cooling tower. The second cooling medium cools the refrigerant vapor in the condenser, and the condenser condenses the refrigerant vapor to a liquid refrigerant. The liquid refrigerant is sent back to the evaporator, and the cycle is then repeated.

In another embodiment, the method for producing cooling comprises producing cooling in a direct expansion chiller as described above with respect to FIG. 3. In this method, a refrigerant composition of the present invention is evaporated in an evaporator. The step of evaporating the refrigerant composition comprises circulating the refrigerant composition through an inlet in the evaporator, through a coil in the evaporator, and through an outlet in the evaporator, thereby lowering the temperature of a first liquid cooling medium contained in the evaporator. The first liquid cooling medium is then passed out of the evaporator to a body to be cooled, thereby producing cooling. The refrigerant vapor is drawn into the compressor, which increases the pressure and the temperature of the refrigerant vapor before it is condensed in a condenser. A second liquid cooling medium is circulated through an inlet in the condenser, through a coil in the condenser, and through an outlet in the condenser. The temperature of the second liquid cooling medium is increased as it passes from the inlet to the outlet of the condenser. The second liquid cooling medium is then sent from the outlet of the condenser to a cooling tower. The refrigerant vapor in the condenser is condensed to refrigerant liquid, and is returned to the evaporator through an expansion valve. The cycle is then repeated.

As noted above, the compositions of the present invention have global warming potentials that are less than many hydrofluorocarbon refrigerants currently in use. The compositions of the present invention have low ozone depletion potential and reduced low global warming potential (GWP) as compared to such currently used hydrocarbon refrigerants. A high GWP refrigerant would be any compound capable of functioning as a refrigerant or heat transfer fluid having a GWP at the 100 year time horizon of about 1000 or greater. One aspect of the present invention is to provide a refrigerant with a global warming potential of less than 1000, less than 500, and in some cases less than 350, or even less than 150, or less than 100, or less than 50, which could be used to replace higher global warming potential refrigerants.

Based upon GWP calculations published by the Intergovernmental Panel on Climate Change (IPCC), Third Assessment Report, the compositions of the present invention are particularly useful for replacing R22, R404A, R407c, R410A or R507A as a working fluid in a stationary heat transfer system, including a stationary air conditioning system or a stationary refrigeration system, or for replacing R22, R407c or R410A in a flooded evaporator chiller or a direct expansion chiller.

Therefore, in accordance with the present invention, there is provided a method for replacing R22, R404A, R407c, R410A or R507A in a stationary air conditioning or refrigeration system. The method comprises providing a refrigerant composition of the present invention to a stationary air conditioning or refrigeration system, in place of R22, R404A, R407c, R410A or R507A.

In addition, in accordance with the present invention, there is provided a method for replacing R-22, R407c or R410A in a flooded evaporator chiller or a direct expansion chiller. The method comprises providing a refrigerant composition of the present invention to a flooded evaporator chiller or a direct expansion chiller in place of R22, R407c or R410A.

In one embodiment of this method, the compositions of the present invention are useful in flooded evaporator chillers that have centrifugal compressors that may have been originally designed and manufactured to operate with R22, R407c or R410A. In another embodiment, the compositions of the present invention are useful in direct expansion chillers that use reciprocating, screw or scroll compressors that may have been originally designed and manufactured to operate with R22, R407c or R410A.

Alternatively, the compositions of the present invention as disclosed herein may be useful in new equipment, such as a new stationary air conditioning or refrigeration system, a new flooded evaporator chiller or a new direct expansion chiller. In such new equipment, either a centrifugal compressor or a positive displacement compressor, including reciprocating, screw or scroll compressors, and the heat exchangers used therewith, could be designed for use with the compositions of the present invention.

EXAMPLES

The sample compositions have the concentrations of components as shown in TABLE 4.

TABLE 4

| Sample # | Concentration (weight fraction) | | | | |
|---|---|---|---|---|---|
| | R32 | R125 | R134a | R290 | $CF_3I$ |
| 1 | 0.500 | | | | 0.500 |
| 2 | 0.600 | | | | 0.400 |
| 3 | 0.400 | | | | 0.600 |
| 4 | 0.700 | | | | 0.300 |
| 5 | | | 0.500 | | 0.500 |
| 6 | | | 0.600 | | 0.400 |
| 7 | | | 0.400 | | 0.600 |
| 8 | | | 0.700 | | 0.300 |
| 9 | 0.700 | | 0.050 | | 0.250 |
| 10 | 0.700 | | 0.250 | | 0.050 |
| 11 | 0.700 | | 0.150 | | 0.150 |
| 12 | 0.600 | | 0.050 | | 0.350 |
| 13 | 0.600 | | 0.350 | | 0.050 |
| 14 | 0.600 | | 0.200 | | 0.200 |
| 15 | 0.500 | | 0.100 | | 0.400 |
| 16 | 0.500 | | 0.400 | | 0.100 |
| 17 | 0.500 | | 0.250 | | 0.250 |
| 18 | 0.330 | | 0.330 | | 0.340 |
| 19 | 0.700 | 0.050 | | | 0.250 |
| 20 | 0.600 | 0.050 | | | 0.350 |
| 21 | 0.500 | 0.050 | | | 0.450 |
| 22 | 0.550 | 0.050 | | 0.050 | 0.350 |
| 23 | 0.600 | 0.025 | | 0.025 | 0.350 |
| 24 | 0.600 | 0.050 | 0.050 | | 0.300 |
| 25 | 0.600 | 0.050 | 0.100 | | 0.250 |
| 26 | 0.500 | 0.050 | 0.050 | | 0.400 |
| 27 | 0.500 | 0.050 | 0.100 | | 0.350 |
| 28 | 0.400 | 0.050 | 0.100 | | 0.450 |
| 29 | 0.400 | 0.050 | 0.050 | | 0.500 |
| 30 | 0.400 | 0.100 | 0.050 | | 0.450 |

Example 1

Refrigeration Performance Data

Table 5 shows cooling performance, as energy efficiency (COP), cooling capacity (Cool Cap), compressor discharge pressure (Dis Press), compressor suction pressure (Suct Press), and compressor discharge temperature (Dis T) for compositions described herein as compared to R507A and R22 (HCFC-22) for low and medium temperature refrigeration systems. Additionally, average temperature glide (Avg glide, which is the average glide for evaporator and compressor) is included. Finally, a GWP value was calculated from the GWP values for the individual components for the 100 year time horizon values.

The data for the present compositions is provided as compared to R507A (a blend of 50 weight % of R125 and 50 weight % R143a (1,1,1-trifluoroethane)), R404A (a blend of 44 weight % of R125, 52 weight % of R143a, and 4.0 weight % of R134a), and R22 (chlorodifluoromethane, CHF$_2$Cl).

The performance data are based on the following conditions:

| | |
|---|---|
| Evaporator temperature | −17.8° C. |
| Condenser temperature | 46.1° C. |
| Subcool temperature | 5.5° C. |
| Return gas temperature | 15.6° C. |
| Compressor efficiency | 70% |

TABLE 5

| Sample # | Calc GWP | Avg Glide (° C.) | COP | Cool Cap (kJ/m3) | Dis Press (kPa) | Suct Press (kPa) | Dis T (° C.) |
|---|---|---|---|---|---|---|---|
| R507A | 3900 | 5.00 | 1.35 | 1801 | 2151 | 342 | 100.0 |
| R404A | 3780 | 0.30 | 1.36 | 1765 | 2104 | 330 | 101.2 |
| R22 | 2000 | 0.00 | 1.46 | 1697 | 1774 | 267 | 144.0 |
| 1 | 276 | 3.00 | 1.36 | 2341 | 2543 | 396 | 159.2 |
| 2 | 330 | 1.27 | 1.36 | 2506 | 2672 | 424 | 162.4 |
| 3 | 221 | 5.95 | 1.38 | 2136 | 2364 | 358 | 155.6 |
| 4 | 385 | 0.47 | 1.36 | 2594 | 2760 | 437 | 166.4 |
| 5 | 651 | 0.09 | 1.50 | 1129 | 1258 | 174 | 108.9 |
| 6 | 780 | 0.18 | 1.50 | 1114 | 1264 | 170 | 108.6 |
| 7 | 521 | 0.34 | 1.51 | 1127 | 1234 | 174 | 109.4 |
| 8 | 910 | 0.34 | 1.50 | 1094 | 1257 | 164 | 108.6 |
| 9 | 450 | 1.02 | 1.36 | 2517 | 2703 | 420 | 165.5 |
| 10 | 710 | 2.89 | 1.38 | 2255 | 2490 | 360 | 161.1 |
| 11 | 580 | 2.04 | 1.37 | 2377 | 2594 | 388 | 163.3 |
| 12 | 395 | 1.58 | 1.37 | 2447 | 2623 | 411 | 160.8 |
| 13 | 785 | 3.79 | 1.39 | 2088 | 2330 | 329 | 154.0 |
| 14 | 590 | 2.79 | 1.38 | 2253 | 2473 | 366 | 157.4 |
| 15 | 405 | 2.79 | 1.38 | 2283 | 2466 | 380 | 154.5 |
| 16 | 795 | 4.30 | 1.40 | 1964 | 2206 | 308 | 148.2 |
| 17 | 600 | 3.53 | 1.39 | 2116 | 2336 | 342 | 151.0 |
| 18 | 611 | 4.50 | 1.42 | 1851 | 2059 | 296 | 139.1 |
| 19 | 555 | 0.32 | 1.36 | 2595 | 2778 | 439 | 164.0 |
| 20 | 500 | 0.09 | 1.36 | 2524 | 2700 | 430 | 159.4 |
| 21 | 445 | 2.29 | 1.36 | 2382 | 2583 | 407 | 155.5 |
| 22 | 474 | 2.27 | 1.34 | 2565 | 2794 | 460 | 149.9 |
| 23 | 416 | 1.60 | 1.35 | 2579 | 2771 | 450 | 156.7 |
| 24 | 565 | 1.34 | 1.37 | 2454 | 2646 | 414 | 158.2 |
| 25 | 630 | 1.81 | 1.37 | 2384 | 2593 | 397 | 157.1 |
| 26 | 510 | 2.25 | 1.37 | 2350 | 2541 | 397 | 153.3 |
| 27 | 575 | 2.45 | 1.38 | 2297 | 2495 | 385 | 151.9 |
| 28 | 520 | 3.65 | 1.39 | 2159 | 2357 | 361 | 146.7 |
| 29 | 456 | 4.01 | 1.37 | 2178 | 2389 | 367 | 148.9 |
| 30 | 625 | 3.24 | 1.37 | 2216 | 2431 | 377 | 145.8 |

Many compositions have similar energy efficiency (COP) as compared to R22, R404A or R507A while maintaining lower discharge pressures and temperatures. Refrigeration capacity for several of the compositions listed in Table 5 is also similar to R22, R404A and R507A, indicating these compositions could be replacement refrigerants for R22, R404A or R507A in stationary air conditioning or stationary refrigeration systems.

Example 2

Air Conditioning Performance Data

Table 6 shows cooling performance, as energy efficiency (COP), cooling capacity (Cool Cap), compressor discharge pressure (Dis Press), compressor suction pressure (Suction Press), and compressor discharge temperature (Dis T) for compositions described herein as compared to R410A and R22 (HCFC-22) for stationary air conditioning systems. Additionally, average temperature glide (Avg glide, which is the average glide for evaporator and compressor) is included. Finally, a GWP value was calculated from the GWP values for the individual components for the 100 year time horizon values.

The data for the present compositions is provided as compared to R410A (a blend of 50 weight % of R125 and 50 weight % of R32), R407c (a blend of 25 weight % of R125, 23 weight % of R32, and 52 weight % of R134a), and R22 (chlorodifluoromethane, CHF$_2$Cl).

The performance data are based on the following conditions:

| | |
|---|---|
| Evaporator temperature | 4° C. |
| Condenser temperature | 43° C. |
| Subcool temperature | 6° C. |
| Return gas temperature | 18° C. |
| Compressor efficiency is | 70% |

TABLE 6

| Sample # | Calc GWP | Avg Glide (° C.) | COP | Cool Cap (kJ/m3) | Dis Press (kPa) | Suct Press (kPa) | Dis T (° C.) |
|---|---|---|---|---|---|---|---|
| R410A | 1700 | 0.10 | 2.72 | 5488 | 2571 | 900 | 90.9 |
| R407C | 1653 | 4.84 | 2.86 | 3855 | 1754 | 564 | 80.6 |
| R22 | 2000 | 0.00 | 2.92 | 3808 | 1648 | 565 | 88.1 |
| 1 | 276 | 3.40 | 2.74 | 5205 | 2366 | 826 | 99.7 |
| 2 | 330 | 1.53 | 2.74 | 5512 | 2486 | 875 | 101.6 |
| 3 | 221 | 6.43 | 2.73 | 4802 | 2198 | 756 | 97.8 |
| 4 | 385 | 0.58 | 2.74 | 5710 | 2566 | 902 | 103.9 |
| 5 | 651 | 0.05 | 2.97 | 2644 | 1166 | 382 | 71.8 |
| 6 | 780 | 0.09 | 2.97 | 2644 | 1170 | 378 | 71.7 |
| 7 | 521 | 0.41 | 2.98 | 2609 | 1144 | 378 | 72.2 |
| 8 | 910 | 0.26 | 2.97 | 2623 | 1162 | 370 | 71.6 |
| 9 | 450 | 1.09 | 2.75 | 5592 | 2513 | 875 | 103.2 |
| 10 | 710 | 2.98 | 2.78 | 5159 | 2310 | 775 | 100.0 |
| 11 | 580 | 2.10 | 2.76 | 5366 | 2410 | 822 | 102.0 |
| 12 | 395 | 1.76 | 2.76 | 5419 | 2439 | 852 | 100.8 |
| 13 | 785 | 3.96 | 2.80 | 4827 | 2161 | 716 | 97.2 |
| 14 | 590 | 2.90 | 2.78 | 5112 | 2297 | 780 | 98.9 |
| 15 | 405 | 3.06 | 2.77 | 5091 | 2293 | 795 | 97.4 |
| 16 | 795 | 4.51 | 2.82 | 4568 | 2045 | 674 | 93.9 |
| 17 | 600 | 3.69 | 2.80 | 4827 | 2168 | 733 | 95.4 |
| 18 | 611 | 4.78 | 2.84 | 4264 | 1911 | 639 | 89.0 |
| 19 | 555 | 0.39 | 2.74 | 5726 | 2583 | 907 | 102.5 |
| 20 | 500 | 1.11 | 2.74 | 5551 | 2511 | 885 | 101.0 |
| 21 | 445 | 2.60 | 2.74 | 5277 | 2403 | 843 | 97.9 |
| 22 | 474 | 2.47 | 2.89 | 5601 | 2603 | 936 | 95.2 |
| 23 | 416 | 1.78 | 2.72 | 5644 | 2581 | 919 | 98.8 |
| 24 | 565 | 1.48 | 2.75 | 5445 | 2461 | 859 | 99.4 |
| 25 | 630 | 1.91 | 2.76 | 5336 | 2410 | 833 | 98.8 |
| 26 | 510 | 2.52 | 2.76 | 5213 | 2363 | 825 | 96.8 |
| 27 | 575 | 2.66 | 2.77 | 5129 | 2320 | 804 | 96.0 |
| 28 | 520 | 4.03 | 2.78 | 4834 | 2191 | 758 | 93.2 |
| 29 | 456 | 4.45 | 2.76 | 4875 | 2222 | 770 | 94.3 |
| 30 | 625 | 3.63 | 2.76 | 4947 | 2261 | 787 | 92.7 |

Many compositions have similar energy efficiency (COP) as compared to R22, R407c or R410A while maintaining lower discharge pressures and temperatures. Refrigeration capacity for several of the compositions listed in Table 6 is also similar to R22, R407c or R410A, indicating these compositions could be replacement refrigerants for R22, R410A or R407c in air-conditioning and chiller systems. Additionally, several of the compositions have low average glide thus allowing use in flooded evaporator type chillers.

What is claimed is:

1. A composition comprising iodotrifluoromethane selected from:
   a. compositions comprising iodotrifluoromethane, difluoromethane, and at least one hydrocarbon selected from the group consisting of pentane, butane, isobutane, propylene, cyclopropylene and propane;
   b. compositions consisting essentially of:
      iodotrifluoromethane and 1,1,1,2-tetrafluoroethane;
      iodotrifluoromethane, 1,1,1,2-tetrafluoroethane and difluoromethane;
      iodotrifluoromethane and pentafluoroethane; or
      iodotrifluoromethane, difluoromethane; pentafluoroethane and 1,1,1,2-tetrafluoroethane;
      or
   c. compositions consisting essentially of about 0.01 to about 67.25 weight difluoromethane and about 32.75 to about 99.99% iodotrifluoromethane.

2. The composition of (a) in claim 1, said composition comprising iodotrifluoromethane, difluoromethane, pentafluoroethane, and propane.

3. The composition of claim 2, comprising:
   35% iodotrifluoromethane, 55% difluoromethane, 5% pentafluoroethane and 5% propane; or
   35% iodotrifluoromethane, 60% difluoromethane, 2.5% pentafluoroethane and 2.5% propane.

4. The composition of claim 1, consisting essentially of:
   30-50 weight percent iodotrifluoromethane and 50-70 weight percent 1,1,1,2-tetrafluoroethane;
   5-35 weight percent iodotrifluoromethane, 5-40 weight percent 1,1,1,2-tetrafluoroethane and 33-70 weight percent difluoromethane; or
   25-50 weight percent iodotrifluoromethane, 40-60 weight percent difluoromethane, 0-50 weight percent pentafluoroethane and 5-50 weight percent 1,1,1,2-tetrafluoroethane.

5. The composition of claim 1 further comprising a lubricant selected from the group consisting of polyalkylene glycols, polyol esters, polyvinylethers, mineral oils, alkylbenzenes, synthetic paraffins, synthetic napthenes, and poly (alpha)olefins.

6. The composition of claim 1 further comprising at least one additive selected from the group consisting of compatibilizers, UV dyes, solubilizing agents, tracers, stabilizers, perfluoropolyethers, and functionalized perfluoropolyethers.

7. A method for producing cooling, comprising evaporating the composition of claim 1 in an evaporator, wherein the composition is a refrigerant, to form a vapor refrigerant, condensing the vapor refrigerant to form a liquid refrigerant, and returning the liquid refrigerant to the evaporator.

8. The method of claim 7, further comprising the step of compressing the refrigerant vapor before it is condensed.

9. The method of claim 7, wherein the cooling is produced in a stationary air conditioning or a stationary refrigeration system.

10. The method of claim 7, further comprising circulating a first cooling medium through an inlet in the evaporator, through a coil in the evaporator and to an outlet of the evaporator, thereby lowering the temperature of the first cooling medium as it passes from the inlet to the outlet of the evaporator, and passing the first cooling medium to a body to be cooled, thereby producing cooling.

11. The method of claim 7, wherein the cooling is produced in a flooded evaporator chiller.

12. The method of claim 7, wherein the step of evaporating the refrigerant composition comprises circulating the refrigerant composition through an inlet in the evaporator, through a coil in the evaporator, and through an outlet in the evaporator, thereby lowering the temperature of a first liquid cooling medium contained in the evaporator, and passing the first liquid cooling medium out of the evaporator to a body to be cooled, thereby producing cooling.

13. The method of claim 12, wherein the cooling is produced in a direct expansion chiller.

14. A method for replacing R22, R407c, R-410A, R404A or R507in a flooded evaporator chiller, a direct expansion chiller or a stationary air conditioning system or a stationary refrigeration system, said method comprising providing a composition of claim 1 to said flooded evaporator chiller, direct expansion chiller or stationary air conditioning or refrigeration system, wherein said composition comprises a refrigerant.

15. The method of claim 14, wherein the refrigerant composition is provided to a stationary air conditioning system or stationary refrigeration system in place of 22, R404A, R407c, R410A or R507A.

16. The method of claim 14, wherein the refrigerant composition is provide to a flooded evaporator chiller or a direct expansion chiller in place of R22, R407c or R410A.

* * * * *